(12) United States Patent
Fu et al.

(10) Patent No.: US 8,085,145 B2
(45) Date of Patent: Dec. 27, 2011

(54) PERSONAL ENVIRONMENTAL MONITORING METHOD AND SYSTEM AND PORTABLE MONITOR FOR USE THEREIN

(75) Inventors: Yongji Fu, Aloha, OR (US); Deepak Ayyagari, Vancouver, WA (US); Nhedti Colquitt, Aloha, OR (US)

(73) Assignee: Sharp Laboratories of America, Inc., Camas, WA (US)

( * ) Notice: Subject to any disclaimer, the term of this patent is extended or adjusted under 35 U.S.C. 154(b) by 356 days.

(21) Appl. No.: 12/384,430

(22) Filed: Apr. 3, 2009

(65) Prior Publication Data

US 2010/0253509 A1 Oct. 7, 2010

(51) Int. Cl.
*G08B 1/08* (2006.01)
(52) U.S. Cl. .................. 340/539.22; 340/521; 340/500; 340/573.1; 600/300; 600/595
(58) Field of Classification Search .................. 340/500, 340/539.22, 539.11, 539.12, 573.1, 539.26; 600/300, 595
See application file for complete search history.

(56) References Cited

U.S. PATENT DOCUMENTS

| | | | | |
|---|---|---|---|---|
| 6,887,201 B2 * | 5/2005 | Bardy | ............................ | 600/300 |
| 6,941,193 B2 | 9/2005 | Frecska et al. | ................ | 700/276 |
| 6,992,580 B2 * | 1/2006 | Kotzin et al. | ............ | 340/539.11 |
| 7,378,954 B2 * | 5/2008 | Wendt | ...................... | 340/539.11 |
| 7,872,574 B2 * | 1/2011 | Betts et al. | ............... | 340/539.26 |
| 7,905,832 B1 * | 3/2011 | Lau et al. | ....................... | 600/300 |
| 2006/0238333 A1 | 10/2006 | Welch et al. | ............. | 340/539.12 |
| 2007/0027367 A1 | 2/2007 | Oliver et al. | .................. | 600/300 |
| 2007/0063850 A1 * | 3/2007 | Devaul et al. | .............. | 340/573.1 |
| 2007/0109119 A1 | 5/2007 | Zhang et al. | ............. | 340/539.22 |
| 2009/0128342 A1 * | 5/2009 | Cohen | ........................ | 340/573.1 |
| 2009/0240120 A1 * | 9/2009 | Mensinger et al. | ........... | 600/301 |

FOREIGN PATENT DOCUMENTS

| | | |
|---|---|---|
| JP | 2003-281694 A | 10/2003 |
| JP | 2006-258460 A | 9/2006 |
| WO | WO2005110208 | 11/2005 |
| WO | WO2005114524 | 12/2005 |

OTHER PUBLICATIONS

A. Pentland, "Healthwear: Medical technology becomes wearable," Computer, 2004, 37(5), 42-49.
S. Koch, "Home telehealth—Current state and future trends," Int'l J. Med. Informatics, 2005, 12 pages.
S. Lee et al., "Development and evaluation of personal respirable particulate sampler (PRPS)," Atmo. Env., 2006, 40(2), 212-24.

* cited by examiner

*Primary Examiner* — Eric M Blount
(74) *Attorney, Agent, or Firm* — Scot A. Reader

(57) ABSTRACT

A personal environmental monitoring method and system and a portable monitor for use therein permit real-time mobile monitoring of environmental conditions in the immediate vicinity to ensure compatibility with the particular environmental sensitivities of a person being monitored. The portable monitor may be a fully integrated mobile device that provides real-time mobile monitoring of immediate environmental conditions without network connectivity.

20 Claims, 7 Drawing Sheets

PERSONAL ENVIRONMENTAL MONITORING METHOD AND SYSTEM AND PORTABLE MONITOR FOR USE THEREIN

BACKGROUND OF THE INVENTION

The present invention relates to personal environmental monitoring and, more particularly, to real-time mobile monitoring of immediate environmental conditions to ensure compatibility with the environmental sensitivities of a person being monitored.

Environmental conditions such as abnormal temperature, abnormal humidity and presence of airborne particles within a certain range of densities can trigger adverse respiratory reactions in individuals that can lead to discomfort, hospitalization and even death. Regional weather and air quality forecasts can provide useful warnings about environmental conditions that may be hazardous to respiratory health. However, regional forecasts are not always accurate. Moreover, environmental conditions in a person's immediate vicinity may be at variance with regional conditions. For example, regional forecasts cannot account for indoor air pollution. Additionally, regional forecasts do not take into account an individual's particular environmental sensitivities. For example, a person with an abnormally high sensitivity to dust is more likely than a person without such sensitivity to experience constricted breathing in an environment with moderate dust particle levels.

Mobile systems that monitor individual respiratory health in real-time based in part on local environmental conditions are known. For example, Ayyagari et al. U.S. application Ser. No. 11/999,569 describes a system in which a portable handset outputs in real-time respiratory health information generated using locally collected environmental and physiological sensor data and patient background information. However, the system calls for configuration of a body area network to collect sensor data. Moreover, the system relies on physiological data such as wheeze rate, crackle rate, pulse rate, respiratory rate, inspiratory duration, expiratory duration and/or SpO2 level to make respiratory health assessments. Also, the patient background information applied in respiratory health assessments does not include a personal environmental profile that addresses the patient's particular environmental sensitivities.

SUMMARY OF THE INVENTION

The present invention provides a personal environmental monitoring method and system and a portable monitor for use therein. The invention permits real-time mobile monitoring of environmental conditions in the immediate vicinity to ensure compatibility with the particular environmental sensitivities of a person being monitored. The invention in some embodiments comprises a fully integrated mobile device that provides real-time mobile monitoring of immediate environmental conditions without network connectivity.

In one aspect of the invention, a portable personal environmental monitor comprises a data acquisition module, a processor communicatively coupled with the data acquisition module and a user interface module communicatively coupled with the processor, wherein under control of the processor the portable monitor continually compares for compatibility a mobile environmental profile generated using sensor data collected by at least one sensor on the data acquisition module and a personal environmental profile generated using inputs received on the user interface module and outputs on the user interface module a personal environmental status indication dynamically regulated based on current compatibility between the mobile environmental profile and the personal environmental profile.

In some embodiments, the personal environmental status indication is dynamically adjusted between a normal indication, a mild alert and a severe alert.

In some embodiments, the portable monitor is a fully integrated device.

In some embodiments, the data acquisition module comprises an airborne particle sensor, a temperature sensor and a humidity sensor.

In some embodiments, the inputs comprise a personal setting for an environmental parameter.

In some embodiments, the environmental parameter is one of airborne particle presence, airborne particle density, ambient temperature or relative humidity.

In some embodiments, the personal environmental profile comprises a personal setting for an environmental parameter, the mobile environmental profile comprises a value for the environmental parameter, and the portable monitor under control of the processor outputs a personal environmental status indication dynamically regulated based on current compatibility between the personal setting and the value.

In some embodiments, the value is a measured value.

In some embodiments, the value is a change rate generated using a plurality of measured values.

In some embodiments, the severe alert includes a change recommendation.

In some embodiments, the portable monitor under control of the processor selects using inputs received on the user interface module a subset of sensors from an environmental sensor suite on the data acquisition module for collecting the sensor data.

In another aspect of the invention, a personal environmental monitoring system comprises a portable environmental data collector and a portable handset wirelessly coupled with the portable environmental data collector, wherein the portable handset continually compares for compatibility a mobile environmental profile generated using sensor data collected by the portable environmental data collector and a personal environmental profile generated using user inputs received on the portable handset and initiates an environmental management action in response to a detected incompatibility.

In some embodiments, the environmental management action comprises outputting an alert on the portable handset.

In some embodiments, the environmental management action comprises transmitting an alert to a remote monitoring server.

In some embodiments, the environmental management action comprises transmitting a command to an environmental control system.

In some embodiments, the environmental management action is specified through a user input on the portable handset.

In some embodiments, the system further comprises an external sensing system wirelessly coupled to the portable handset and the mobile environmental profile is further generated using sensor data collected by the external sensing system.

In some embodiments, the portable handset transmits to the portable environmental data collector sensor selection information generated using a user input on the portable handset and the portable environmental data collector selects using the sensor selection information a subset of sensors from an environmental sensor suite on the portable environmental data collector for collecting the sensor data.

In yet another aspect of the invention, a personal environmental monitoring method comprises the steps of generating a personal environmental profile using user inputs, generating a mobile environmental profile using sensor data, continually comparing for compatibility the mobile environmental profile and the personal environmental profile and initiating an environmental management action in response to a detected incompatibility.

These and other aspects of the invention will be better understood by reference to the following detailed description taken in conjunction with the drawings that are briefly described below. Of course, the invention is defined by the appended claims.

DETAILED DESCRIPTION OF A PREFERRED EMBODIMENT

Figure 1:
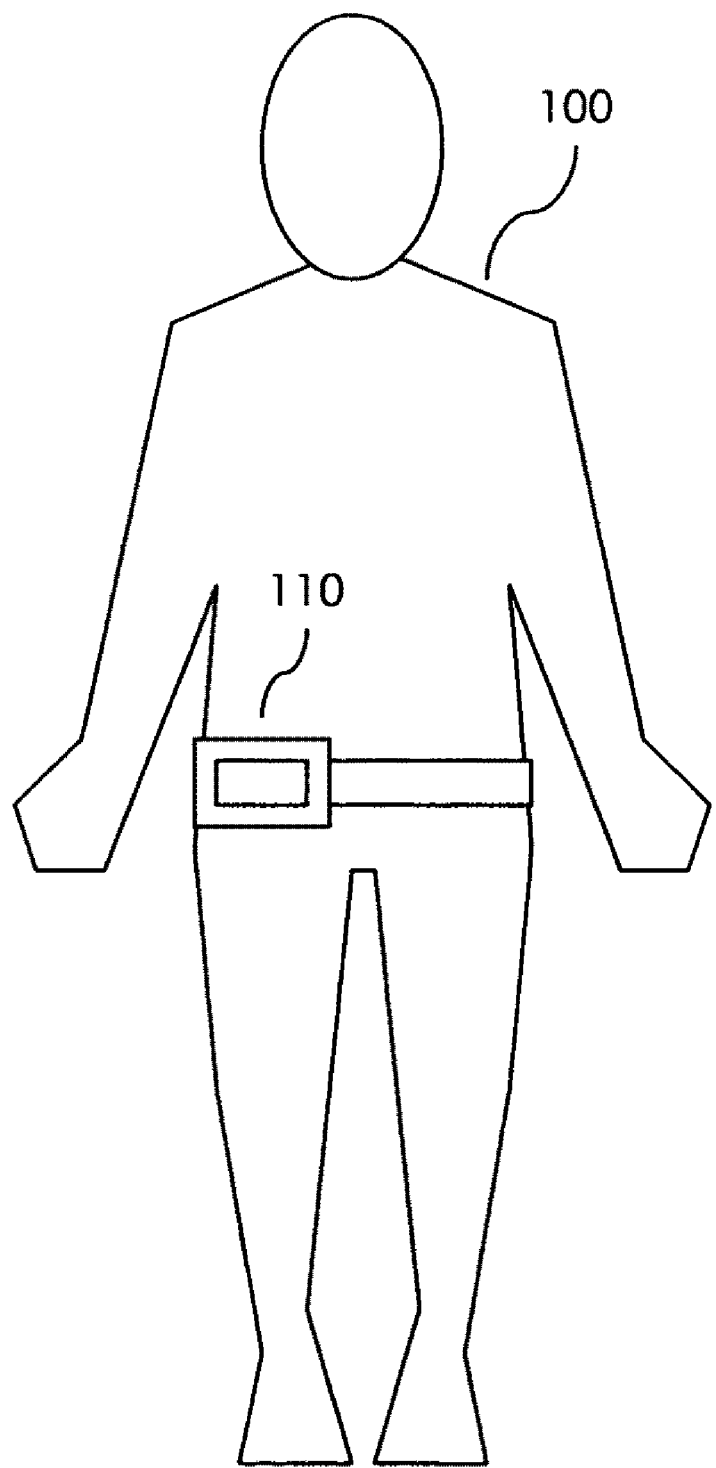
FIG. 1 shows a portable personal environmental monitor in some embodiments of the invention.

FIG. 1 shows a portable personal environmental monitor 110 in some embodiments of the invention. Portable monitor 110 is a fully integrated consumer electronics device wherein the electronics components reside within an enclosure. The enclosure may be water resistant to shield the electronics components from moisture intrusion. Portable monitor 110 is not networked during normal operation. Portable monitor 110 is shown attached at the waist of a user 100 being monitored, although in other embodiments monitor 110 may be positioned at a different body location or hand-held.

Figure 2:
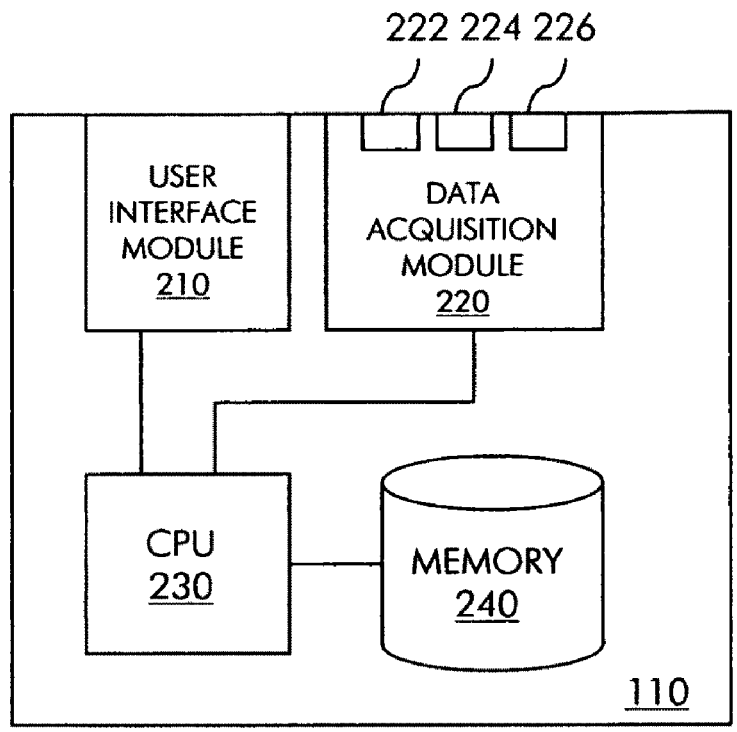
FIG. 2 shows the portable monitor of FIG. 1 in more detail.

FIG. 2 shows portable monitor 10 in more detail. Portable monitor 10 includes a user interface module 210 adapted to receive inputs and render outputs to user 100. User interface module 210 includes a keypad, touch screen and/or microphone for receiving inputs and a display, such as a liquid crystal display (LCD) or light emitting diode (LED) display, and a loudspeaker for rendering outputs.

Portable monitor 110 further includes a data acquisition module 220. Data acquisition module 220 includes an environmental sensor suite having a multiple of sensors 222, 224, 226 for measuring a respective multiple of different environmental parameters. An airborne particle sensor 222 detects particle presence and/or measures particle density (e.g. in units of milligrams per cubic centimeter or number of particles per cubic meter). In some embodiments, airborne particle sensor 222 measures particle density for several ranges of particle sizes. In other embodiments, airborne particle sensor 222 measures overall particle density without regard to particle sizes. The particle sensor marketed by Sharp Electronics Corporation as part number GP2Y1010AU and/or the particle sensor marketed by Shinyei Corporation as part number PPD3NS may be used, by way of example. A temperature sensor 224 measures ambient temperature. The temperature sensor marketed by Canadian Thermostats & Control Devices, Ltd. (Cantherm) as part number MF51E103F3950C may be used, by way of example. A humidity sensor 226 measures relative humidity. The humidity sensor marketed by Measurement Specialties, Inc. as part number HTS2030SMD may be used, by way of example. Data acquisition module 220 also includes circuits to facilitate sensing and data reporting operations, such as a driver/controller, amplifiers, front-end filters and one or more A/D converters.

Portable monitor 110 further includes a memory 240 adapted to store software, settings and data. In some embodiments, memory 240 includes one or more random access memory (RAM) and one or more read only memory (ROM) elements.

Portable monitor 110 further has a processor 230 communicatively coupled between elements 210, 220, 240. Processor 230 is adapted to execute software stored in memory 240, reference settings and data, and interoperate with elements 210, 220, 240 to perform the various features and functions supported by portable monitor 110. In some embodiments, processor 230 is a microcontroller.

Figure 3:
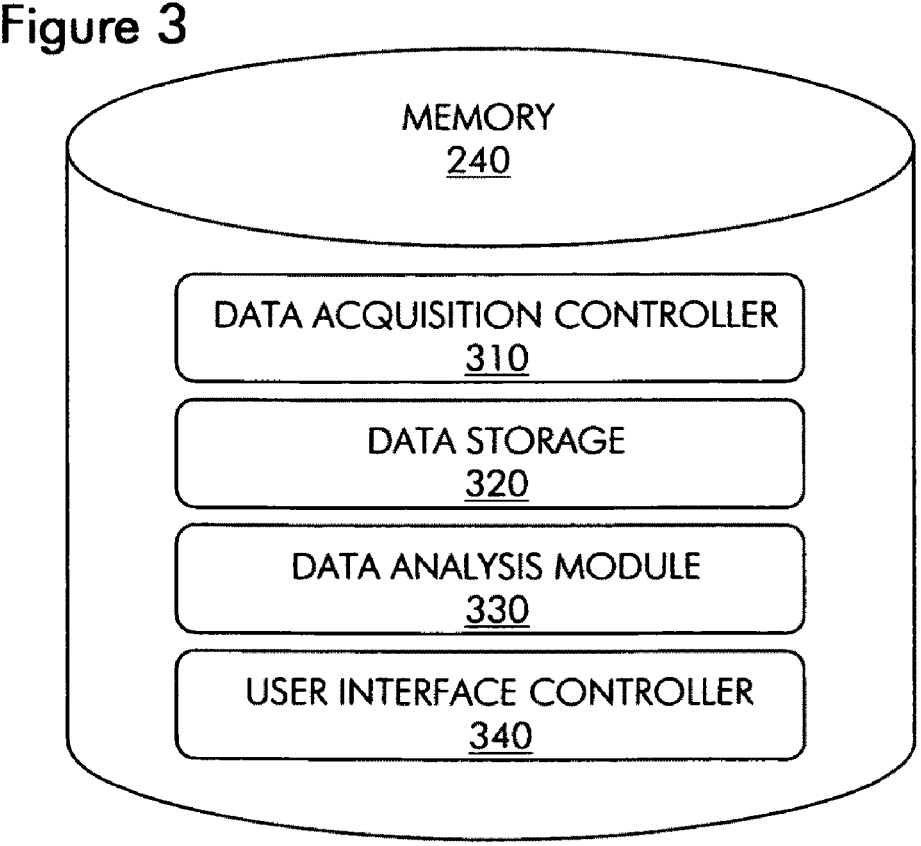
FIG. 3 shows operational elements of the portable monitor of FIG. 1.

FIG. 3 shows elements of portable monitor 110 operative to facilitate personal environmental monitoring in some embodiments of the invention. The elements include a data acquisition controller 310, data storage 320, a data analysis module 330 and a user interface controller 340. Modules 310, 330, 340 are software programs having instructions executable by processor 230 to generate a personal environmental profile for user 100 using personal environmental settings received on user interface module 210, generate a mobile environmental profile using environmental sensor data received from data acquisition module 220, store and retrieve data to and from data storage 320, manipulate such data, dynamically regulate a personal environmental status indication based on current compatibility of user 100 with immediate environmental conditions and output the personal environmental status indication on user interface module 210.

User interface controller 340 receives personal environmental settings and stores them in data storage 320. Personal environmental settings are configured through inputs by user 100 on user interface module 210. Personal environmental settings may specify tolerable conditions, thresholds and/or change rates for environmental parameters that if violated trigger environmental alerts. Personal environmental settings may be chosen in accordance with the particular environmental sensitivities of user 100, that is, specify a tolerable environment for user 100 that if unmet would be expected based on the post experience of user 100 to adversely impact the health of user 100. Personal environmental settings may include, for example, airborne particle presence (i.e. a Boolean data type threshold), maximum airborne particle density, maximum airborne particle density change rate, maximum airborne particle size, minimum ambient temperature, maximum ambient temperature, maximum ambient temperature change rate, minimum relative humidity, maximum relative humidity and maximum relative humidity change rate. In some embodiments, separate settings may be configured for different types of airborne particles, for example, maximum dust particle density and maximum smoke particle density.

Data acquisition controller 310 receives environmental sensor data and stores them in data storage 320. Environmental sensor data is continually received from data acquisition module 220. Data acquisition controller 310 may poll data acquisition module 220 at a polling interval configured on portable monitor 110 to acquire environmental sensor data. Acquired environmental sensor data may include, for example, airborne particle presence data, airborne particle density data, ambient temperature data and relative humidity data. Data acquisition controller 310 acquires environmental sensor data from data acquisition module 220 with sufficient frequency to ensure that the compatibility of immediate environmental conditions with the particular environmental sensitivities of user 100 can be accurately determined at all times. In some embodiments, data acquisition controller 310 determines one or more of particle size and/or particle type using environmental sensor data received from airborne particle sensor 222 by employing teachings of U.S. application Ser. No. 12/384,368, published as U.S. Patent Application Pub. No. 2010/0253943, entitled "Methods and Systems for Particle Characterization Using Optical Sensor Output Signal Fluctuation," filed on the same date and shoring a common assignee with this application, and which is incorporated herein by reference.

Data analysis module 330 generates a personal environmental profile for user 100 using the personal environmental settings stored in data storage 320. The personal environmental profile includes one or more settings for one or more environmental parameters. The settings may establish, for example, a condition, a minimum value, a maximum value, a minimum change rate or a maximum change rate for an environmental parameter. The environmental parameters may include, for example, airborne particle presence, airborne particle density, ambient temperature or relative humidity. Data analysis module 330 stores the personal environmental profile in data storage 320.

Data analysis module 330 also generates and regularly updates a mobile environmental profile using the environmental sensor data stored in data storage 320. The mobile environmental profile includes measured values and/or change rates for environmental parameters. Data analysis module 330 may utilize for the mobile environmental profile moving averages or weighted moving averages of values instead of instantaneous values in order to smooth the data and reduce false alarms. Data analysis module 330 also performs preprocessing functions necessary to convert environmental sensor data into a form suitable for analysis. Data analysis module 330 stores the mobile environmental profile in data storage 320.

Data analysis module 330 continually compares for compatibility the personal environmental profile and mobile environmental profile and dynamically regulates a personal environmental status indication based on a current state of compatibility between the profiles. In some embodiments, the personal environmental status indication is dynamically adjusted between a normal indication, a mild alert and a severe alert. Depending on user configuration, the personal environmental status indication may be dynamically regulated based on current compatibility with one personal environmental setting or a designated combination of personal environmental settings. For example, data analysis module 330 may output a mild alert upon determining that a measured value or change rate for one or more of airborne particle presence, airborne particle density, ambient temperature or relative humidity has violated a personal environmental setting set by user 100 for the corresponding measured value or change rate to a first degree, and output a severe alert upon determining that the measured value or change rate has violated the personal environmental setting to a second degree that is larger than the first degree. Alternatively, data analysis module 330 may output a mild alert upon determining that a measured value or change rate is close to violating a personal environmental setting is near, and may output a severe alert upon determining that a measured value or change rate has violated a personal environmental setting. In the absence of any alert, data analysis module 330 outputs a normal indication. Alerts may include text messages. An alert text message may identify the reason for the alert (e.g. "humidity too low") and make a change recommendation (e.g. "leave this environment," "turn on humidifier").

Additionally, the visual component of personal environmental status indications may be color-coded. For example, a normal indication may be displayed in green, a mild alert may be displayed in yellow and a severe alert may be displayed in red.

User interface controller 340 continually outputs on user interface module 210 mobile environmental profile data. Outputted mobile environmental profile data may include conditions and instantaneous (or moving average) measured values and change rates for environmental parameters, such as airborne particle presence, airborne particle density, temperature and humidity.

User interface controller 340 also continually outputs on user interface module 210 personal environmental status indications, which include normal indications, mild alerts and severe alerts depending on current compatibility of the personal environmental profile and the mobile environmental profile. An alert may include an audible, tactile (e.g. vibration) and/or visual alarm as well as a text message that indicates the reason for the alert and makes an environmental change recommendation.

Figure 4:
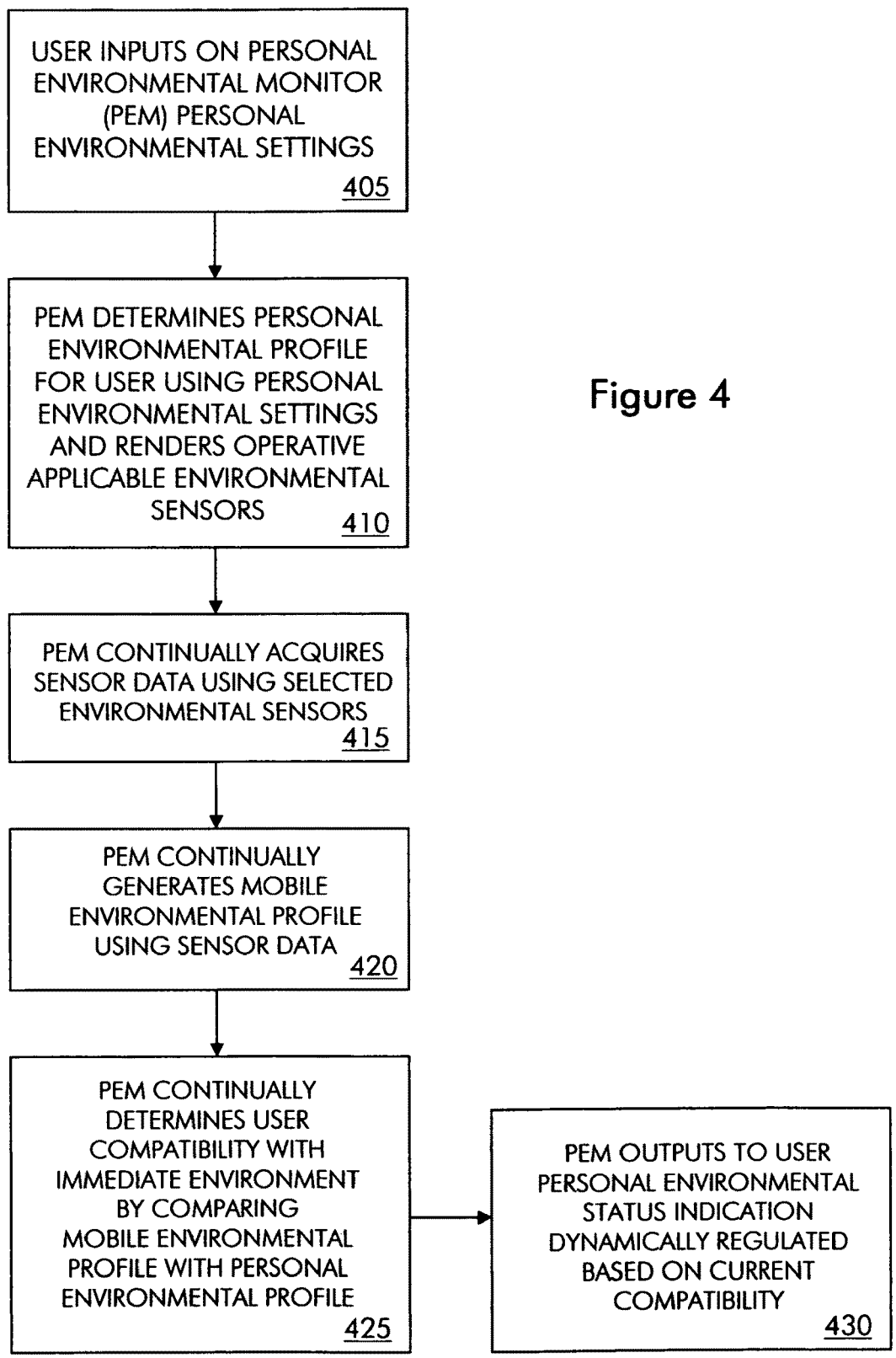
FIG. 4 shows a personal environmental monitoring method performed by the portable monitor of FIG. 1.

FIG. 4 shows a personal environmental monitoring method performed by portable monitor 10. User 100 inputs on user interface module 210 one or more personal environmental settings (405). Portable monitor 110 under control of processor 230 generates a personal environmental profile using the personal environmental settings and renders operative selected ones of sensors 222, 224, 226 from the environmental sensor suite on data acquisition module 220 that correspond to the personal environmental settings (410). For example, if user 100 inputs an airborne particle density setting in the absence of any other setting, only airborne particulate sensor 222 is rendered operative. Operative ones of sensors 222, 224, 226 then collect environmental sensor data which are continually relayed to processor 230 for analysis (415). Portable monitor 10 under control of processor 230 generates a mobile environmental profile using the sensor data (420). Portable monitor 110 under control of processor 230 then determines the compatibility of user 100 with the immediate environment by comparing the mobile environmental profile with the personal environmental profile (425). Portable monitor 110 under control of processor 230 then outputs a personal environmental status indication based on current compatibility (430). If an incompatibility is detected, portable monitor 110 under control of processor 230 outputs to user 100 via user interface module 210 an alert, which may be a severe or mild alert, and may include a change recommendation.

Figure 5:
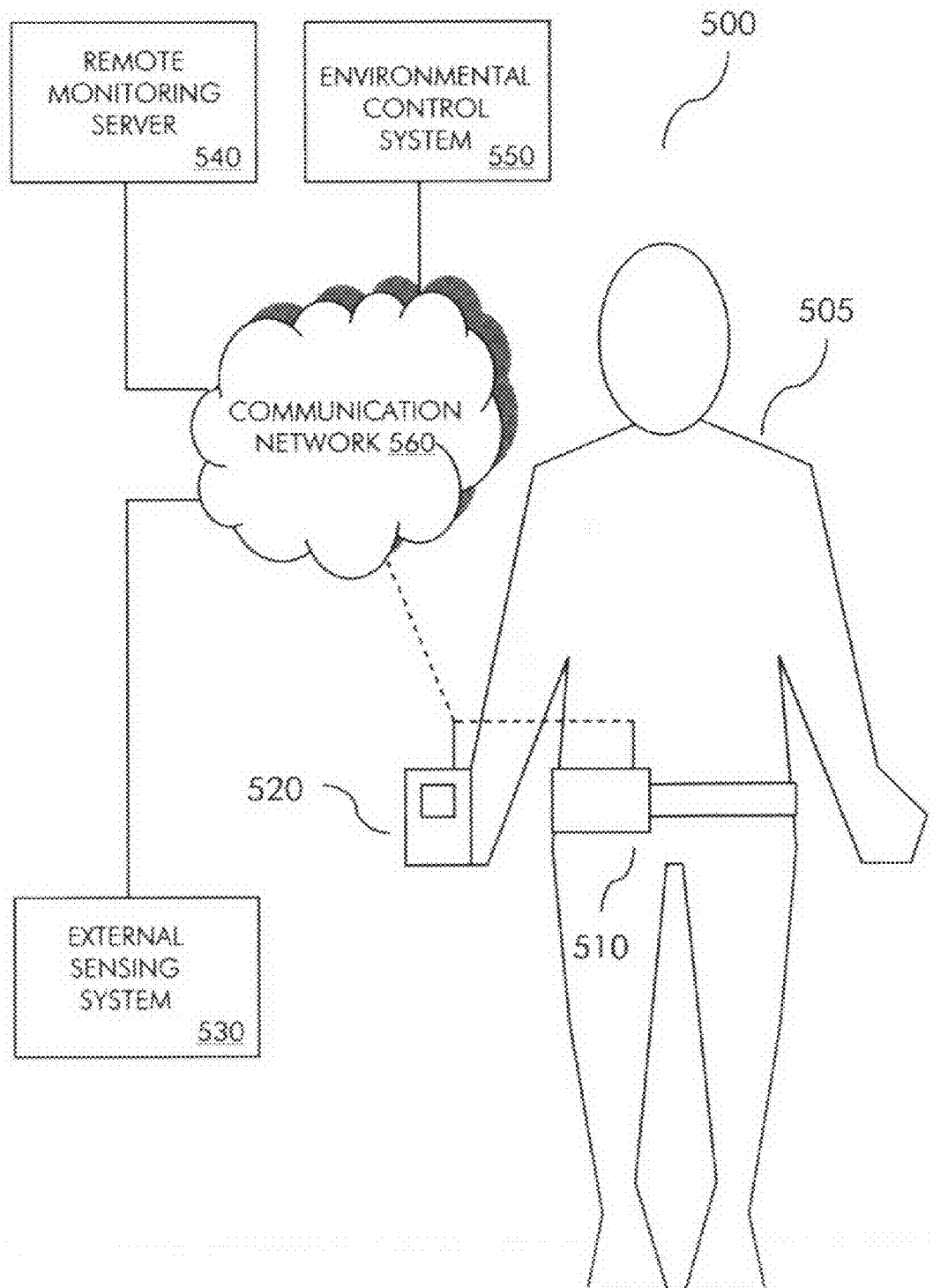
FIG. 5 shows a personal environmental monitoring system in some embodiments of the invention.

FIG. 5 shows a personal environmental monitoring system 500 in some embodiments of the invention. In these embodiments, a computer network enables sharing of system processing burdens and support for value-added features, such as integration of external environmental sensor data, clinical review of system data and automatic regulation of the local environment. System 500 includes a portable environmental data collector 510. Collector 510 is shown attached at the waist of a user 505 being monitored, although in other embodiments collector 510 may be positioned at a different body location or hand-held. Collector 510 is wirelessly coupled with a portable handset 520 in the immediate vicinity of a user 505 via Bluetooth or other short range communication protocol. Handset 520 is in turn is communicatively coupled with a remote monitoring server 540 via a communication network 560. Handset 520 is also communicatively coupled with an external sensing system 530 and environmental control system 550, either via communication network 560 (as shown) or via direct wireless links.

Figure 6:
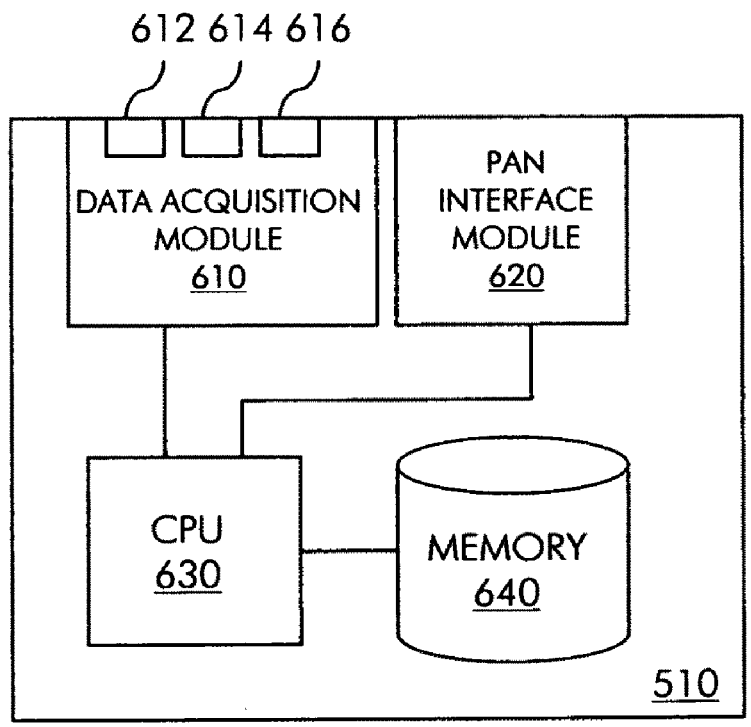
FIG. 6 shows the portable environmental data collector from FIG. 5 in more detail.

FIG. 6 shows collector 510 in more detail. Collector 510 has a data acquisition module 610. Data acquisition module 610 includes an environmental sensor suite having a multiple of sensors 612, 614, 616 for measuring a respective multiple of different environmental parameters. Data acquisition module 610 includes an airborne particle sensor 612 that detects particle presence and/or measures particle density, a temperature sensor 614 that measures ambient temperature and a humidity sensor 616 that measures relative humidity. Data acquisition module 220 also includes circuits to facilitate sensing and data reporting operations, such as a driver/controller, amplifiers, front-end filters and one or more A/D converters.

Collector 510 further includes a personal area network (PAN) interface module 620. PAN interface module 620 has a short range wireless interface, such as a Bluetooth interface, for exchanging data with handset 520 via a wireless link.

Collector 510 also includes a memory 640 adapted to store software, settings and data. In some embodiments, memory 640 includes one or more RAM and one or more ROM elements.

Collector 510 further has a processor 630 communicatively coupled between elements 610, 620, 640. Processor 630 is adapted to execute software stored in memory 640, reference settings and data, and interoperate with elements 610, 620, 640 to perform various features and functions supported by collector 510. In some embodiments, processor 630 is a microcontroller.

Figure 7:
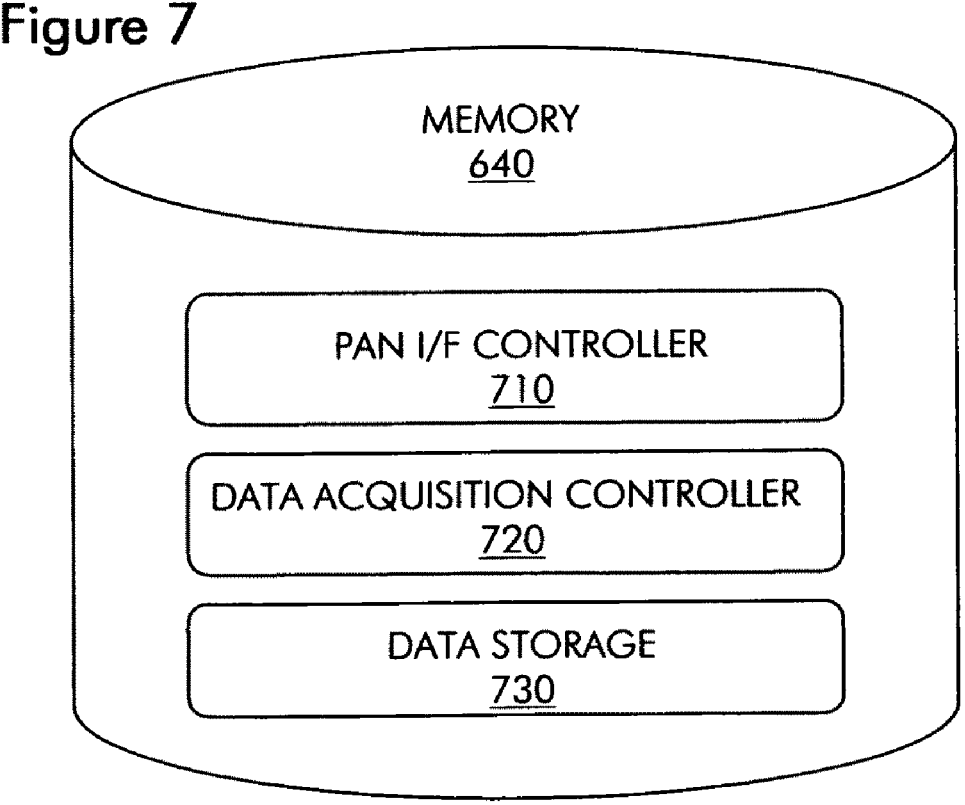
FIG. 7 shows operational elements of the portable environmental data collector from FIG. 5.

FIG. 7 shows elements of collector 510 operative to facilitate personal environmental monitoring in some embodiments of the invention. The elements include a PAN interface controller 710, a data acquisition controller 720 and data storage 730. Elements 710, 720 are software programs having instructions executable by processor 630 to interface with handset 520 to render operative ones of sensors 612, 614, 616 for collecting environmental data, receive and store in data storage 730 environmental sensor data collected by operative sensors and retrieve from data storage 730 and transmit to handset 520 environmental data collected by operative sensors.

PAN interface controller 710 manages on behalf of collector 510 a short range wireless link, such as a Bluetooth link, between collector 510 and handset 520, including link establishment and tear-down, data formatting and data conversions.

Data acquisition controller 720 receives environmental sensor data and stores them in data storage 730. Environmental sensor data are continually received from data acquisition module 610. Data acquisition module 720 may poll data acquisition module 610 at a polling interval configured on collector 510 to acquire environmental sensor data. Acquired environmental sensor data may include, for example, airborne particle presence data, airborne particle density data, ambient temperature data and relative humidity data.

Handset 520 is a handheld mobile electronic device operated by user 505. Handset 520 may be a multipurpose device, such as a cellular phone, personal data assistant (PDA), Internet appliance, media player (e.g. IPod), or may be a device that is specially designed for use within personal environmental monitoring system 500.

Figure 8:
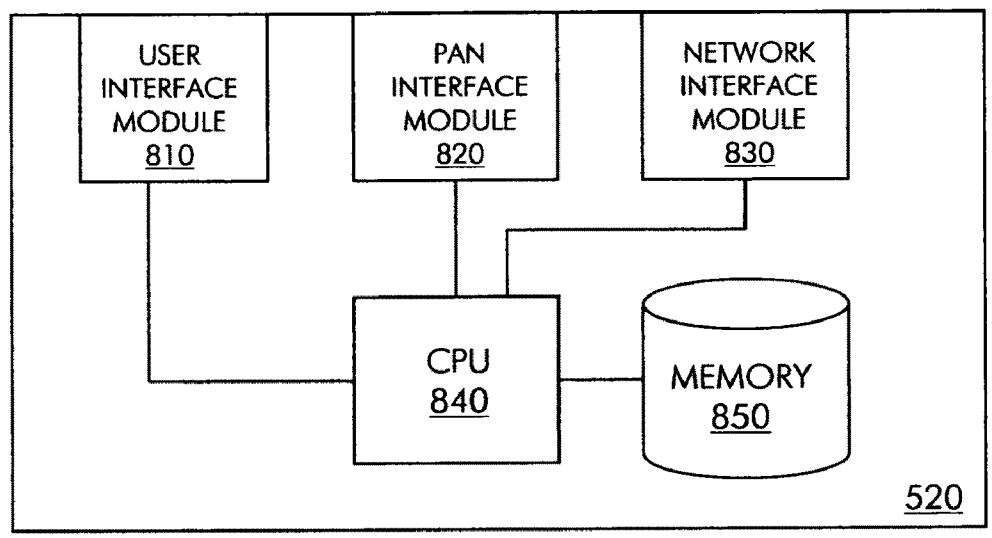
FIG. 8 shows portable handset from FIG. 5 in more detail.

FIG. 8 shows handset 520 in more detail. Handset 520 includes a user interface 810 adopted to receive inputs and render outputs to user 505. User interface 810 includes a keypad, touch screen and/or microphone for receiving inputs and a display, such as a LCD or LED display, and a loudspeaker for rendering outputs.

Handset 520 further includes a PAN interface module 820. PAN interface module 820 has a short range wireless interface, such as a Bluetooth interface, for exchanging data with portable collector 510 via a wireless link.

Handset 520 further includes a network interface module 830. Network interface module 880 has one or more wireless interfaces, such as wireless LAN or cellular interfaces, for exchanging data with remote monitoring server 540 via communication network 560 and with external sensing system 530 and environmental control system 550 either via communication network 560 or direct wireless links.

Handset 520 further includes a memory 850 adapted to store software, settings and data. In some embodiments, memory 850 includes one or more RAM and one or more ROM elements.

Handset 520 further has a processor 840 communicatively coupled between elements 810, 820, 830, 850. Processor 840 is adapted to execute software stored in memory 850, reference settings and data, and interoperate with elements 810, 820, 830, 850 to perform various features and functions supported by handset 520.

Figure 9:
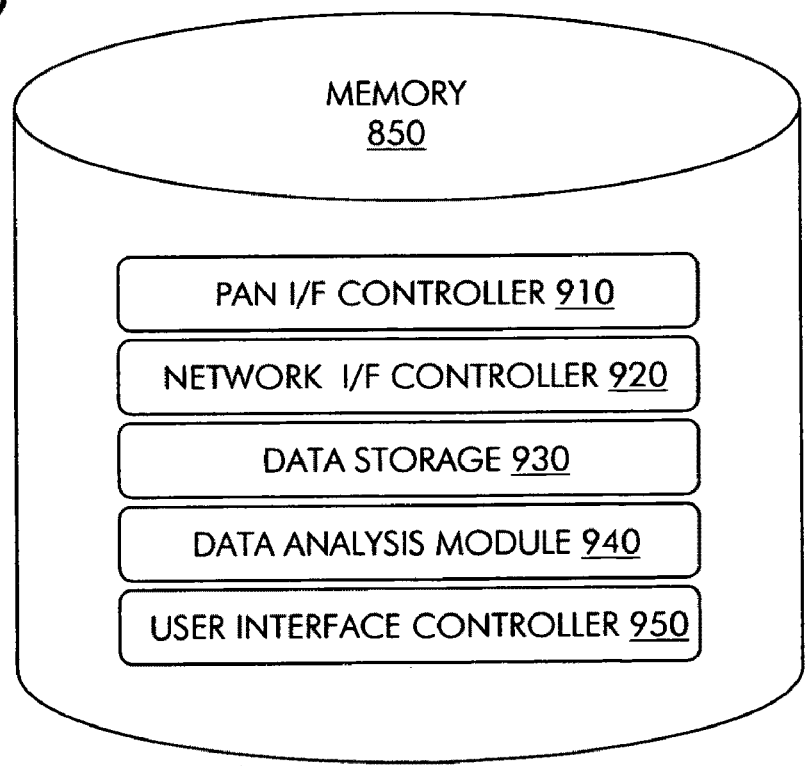
FIG. 9 shows operational elements of the portable handset from FIG. 5.

FIG. 9 shows elements of handset 520 operative to facilitate personal environmental monitoring in some embodiments of the invention. The elements include a PAN interface controller 910, a network interface controller 920, data storage 930, a data analysis module 940 and a user interface controller 950. Elements 910, 920, 940, 950 are software programs having instructions executable by processor 840 to generated personal environmental profile for user 505 using personal environmental settings received on user interface module 810, generate a mobile environmental profile using environmental sensor data received from collector 510 via PAN interface module 820, store and retrieve data to and from data storage 930, manipulate such data and initiate specified actions in response to a detected incompatibility of user 505 with local environmental conditions.

PAN interface controller 910 manages on behalf of handset 520 a wireless link between collector 510 and handset 520, including link establishment and tear-down, data formatting and data conversions. PAN interface controller 910 also stores in data storage 930 environmental data received from collector 510 via PAN interface module 820.

Network interface controller 920 manages on behalf of handset 520 a wireless link between handset 520 and communication network 560, including link establishment and tear-down, data formatting and conversions, as well as managing any other wireless links to external sensing system 530 and/or environmental control system 550.

User interface controller 950 receives personal environmental settings and stores them in data storage 930. Personal environmental settings are configured through inputs by user 505 on user interface module 810. Personal environmental settings may specify tolerable conditions, thresholds and/or change rates for environmental parameters that if violated trigger environmental alerts. Personal environmental settings may be chosen in accordance with the particular environmental sensitivities of user 505. Personal environmental settings may include, for example, airborne particle presence (i.e. a Boolean data type threshold), maximum airborne particle density, maximum airborne particle density change rate, minimum ambient temperature, maximum ambient temperature, maximum ambient temperature change rate, minimum relative humidity, maximum relative humidity and maximum relative humidity change rate. In some embodiments, separate settings may be configured for different types of airborne particles, for example, dust and smoke.

Data analysis module 940 generates a personal environmental profile for user 505 using the personal environmental settings stored in data storage 930. The personal environmental profile includes one or more settings for one or more environmental parameters. The settings may establish, for example, a condition, a minimum value, a maximum value, a minimum change rate or a maximum change rate for an environmental parameter. The environmental parameters may include, for example, airborne particle presence, airborne particle density, ambient temperature or relative humidity. Data analysis module 940 stores the personal environmental profile in data storage 930.

Data analysis module 940 also generates and regularly updates a mobile environmental profile using environmental sensor data received from collector 510 and stored in data storage 930. The mobile environmental profile includes measured values and/or change rates for environmental parameters. Data analysis module 940 may utilize for the mobile environmental profile moving averages or weighted moving averages of values instead of instantaneous values in order to smooth the data and reduce false alarms. Data analysis module 940 also performs preprocessing functions necessary to convert environmental sensor data into a form suitable for analysis. Data analysis module 940 stores the mobile environmental profile in data storage 930.

Data analysis module 940 further continually compares for compatibility the personal environmental profile and mobile environmental profile and initiates one or more specified actions in response to a detected incompatibility. Specified actions may include, for example, generating an environmental alert for outputting on user interface module 810, generating an environmental alert for transmitting to remote monitoring server 540 for clinician analysis and generating a command for transmitting to environmental control system 550 for automatically regulating the local environment (e.g. controlling a thermostat or humidifier) in an attempt to eliminate the incompatibility.

User interface controller 950 continually outputs on user interface module 810 mobile environmental profile data. Outputted mobile environmental profile data may include conditions and instantaneous (or moving average) measured values and change rates for environmental parameters, such as airborne particle presence, airborne particle density, temperature and humidity.

User interface controller 950 also outputs on user interface module 810 event-driven environmental alerts. An environmental alert includes an audible, tactile (e.g. vibration) and/or visual alarm as well as a text message that indicates the reason for the alert and makes a change recommendation.

External sensing system 530 is a system local to user 505 that measures and reports one or more environmental parameters. For example, external sensing system 530 may be an air purifier that senses dust or a wireless weather station that senses ambient temperature and/or relative humidity, and reports environmental data to handset 520 via network interface module 830.

Remote monitoring server 540 is a computing device accessible by a secondary user, such as the user's allergist or other clinician, to extract data uploaded from portable handset 520 for review and analysis. In some embodiments, remote monitoring server 540 also allows a clinician to download to handset 520 data, such as a modified personal environmental profile generated in response to an environmental alert.

Environmental control system 550 is a system adapted to regulate the indoor environment where user 505 is located. Environment control system 550 may be an air conditioning, heating, humidification or ventilation system, for example.

Communication network 560 is a data communication network that may include one or more wired or wireless LANs, WANs, WiMAX networks, USB networks, cellular networks and/or ad-hoc networks each of which may have one or more data communication nodes, such as switches, routers, bridges, hubs, access points or base stations, operative to communicatively couple handset 520 with remote monitoring server 530 and environment control system 550. In some embodiments, communication network 560 traverses the Internet.

Figure 10:
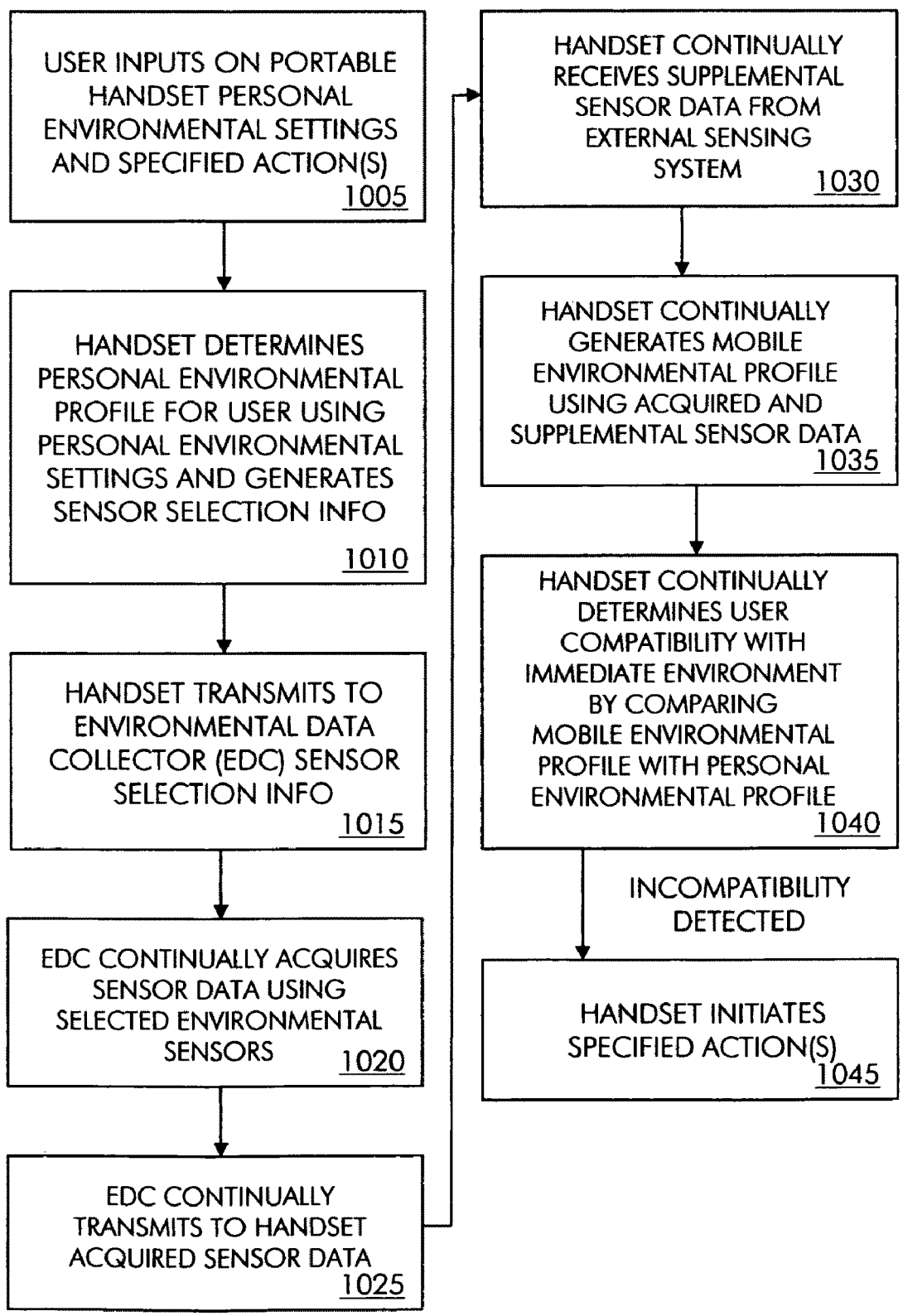
FIG. 10 shows a personal environmental monitoring method performed in the personal environmental monitoring system of FIG. 5.

FIG. 10 shows a personal environmental monitoring method performed in personal environmental monitoring system 500. User 505 inputs on handset 520 one or more personal environmental settings and one or more specified actions (1005). Handset 520 generates a personal environmental profile using the personal environmental settings, selects ones of sensors 612, 614, 616 on collector 510 that must be rendered operative to verify compliance with the personal environmental settings and generates sensor selection information (1010). Handset 520 transmits the sensor selection information to collector 510 via PAN interface module 820 (1015). Collector 510 receives the sensor selection information via PAN interface module 620 and renders operative the selected ones of sensors 612, 614, 616. The selected ones of sensors 612, 614,616 then collect environmental sensor data (1020) and the data are continually relayed to handset 520 via PAN interface 820 for analysis (1025). Handset 520 also separately receives supplemental environmental sensor data from external sensing system 530 (1030). Handset 520 generates a mobile environmental profile using the sensor data (1035). Handset 520 then determines the compatibility of user 505 with the local environment by comparing the mobile environmental profile with the personal environmental profile (1040). If an incompatibility is detected, handset 520 initiates one or more specified actions, such as generating and outputting on user interface module 810 an environmental alert, generating and transmitting to remote monitoring server 540 for clinician analysis an environmental alert and/or generating and transmitting to environmental control system 550 a command for automatically regulating the environment (e.g. controlling a thermostat or humidifier) in an attempt to eliminate the incompatibility.

It will be appreciated by those of ordinary skill in the art that the invention can be embodied in other specific forms without departing from the spirit or essential character hereof. The present description is therefore considered in all respects to be illustrative and not restrictive. The scope of the invention is indicated by the appended claims, and all changes that come with in the meaning and range of equivalents thereof are intended to be embraced therein.

What is claimed is:

1. A portable personal environmental monitor, comprising:
 a data acquisition module;
 a processor communicatively coupled with the data acquisition module; and
 a user interface module communicatively coupled with the processor, wherein under control of the processor the portable monitor continually compares for compatibility a mobile environmental profile generated using sensor data collected by at least one sensor on the data acquisition module and a personal environmental profile generated using inputs received on the user interface module and outputs on the user interface module a personal environmental status indication dynamically regulated based on current compatibility between the mobile environmental profile and the personal environmental profile, wherein in response to finding an incompatibility between the mobile environmental profile and the personal environmental profile the personal environmental status indication outputted on the user interface module includes a text message recommending a specific user action to address the incompatibility.

2. The portable monitor of claim 1, wherein the personal environmental status indication is dynamically adjusted between a normal indication, a mild alert and a severe alert.

3. The portable monitor of claim 1, wherein the portable monitor is a fully integrated device.

4. The portable monitor of claim 1, wherein the data acquisition module comprises an airborne particle sensor, a temperature sensor and a humidity sensor.

5. The portable monitor of claim 1, wherein the inputs comprise a personal setting for an environmental parameter.

6. The portable monitor of claim 5, wherein the environmental parameter is one of airborne particle presence, airborne particle density, ambient temperature or relative humidity.

7. The portable monitor of claim 1, wherein the personal environmental profile comprises a personal setting for an environmental parameter, the mobile environmental profile comprises a value for the environmental parameter, and the portable monitor under control of the processor outputs a personal environmental status indication dynamically regulated based on current compatibility between the personal setting and the value.

8. The portable monitor of claim 7, wherein the value is a measured value.

9. The portable monitor of claim 7, wherein the value is a change rate generated using a plurality of measured values.

10. The portable monitor of claim 1, wherein the portable monitor under control of the processor selects using inputs received on the user interface a subset of sensors from an environmental sensor suite on the data acquisition module for collecting the sensor data.

11. A personal environmental monitoring system, comprising:

a portable environmental data collector; and a portable handset wirelessly coupled with the portable environmental data collector, wherein the portable handset continually compares for compatibility a mobile environmental profile generated using sensor data collected by the portable environmental data collector and a personal environmental profile generated using user inputs received on the portable handset and initiates an environmental management action in response to a detected incompatibility whereby an indoor environment where the portable handset is located is automatically controlled.

12. The monitoring system of claim 11, wherein the environmental management action comprises outputting an alert on the portable handset.

13. The monitoring system of claim 11, wherein environmental management action comprises transmitting an alert to a remote monitoring server.

14. The monitoring system of claim 11, wherein the environmental management action comprises transmitting a command to an environmental control system.

15. The monitoring system of claim 11, wherein the environmental management action is specified through a user input on the portable handset.

16. The monitoring system of claim 11, wherein the system further comprises an external sensing system wirelessly coupled to the portable handset and the mobile environmental profile is further generated using sensor data collected by the external sensing system.

17. The monitoring system of claim 11, wherein the portable handset transmits to the portable environmental data collector sensor selection information generated using a user input on the portable handset and the portable environmental data collector selects using the sensor selection information a subset of sensors from an environmental sensor suite on the portable environmental data collector for collecting the sensor data.

18. The system of claim 11, wherein the indoor environment is automatically controlled at least in part by activating an air conditioning system.

19. The system of claim 11, wherein the indoor environment is automatically controlled at least in part by activating a humidification system.

20. The system of claim 11, wherein the indoor environment is automatically controlled at least in part by activating a ventilation system.

* * * * *